United States Patent
Lee et al.

(10) Patent No.: US 10,105,465 B2
(45) Date of Patent: Oct. 23, 2018

(54) BIODEGRADABLE MEDICAL ADHESIVE OR SEALANT COMPOSITION

(71) Applicant: UTAH-INHA DDS & ADVANCED THERAPEUTICS RESEARCH CENTER, Incheon (KR)

(72) Inventors: Eunhye Lee, Incheon (KR); Jin Hee Maeng, Bucheon-si (KR); Keun Su Kim, Incheon (KR); Don Haeng Lee, Seoul (KR); Young Hwan Park, Wonju-si (KR)

(73) Assignee: UTAH-INHA DDS & ADVANCED THERAPEUTICS RESEARCH CENTER, Incheon (KR)

( * ) Notice: Subject to any disclaimer, the term of this patent is extended or adjusted under 35 U.S.C. 154(b) by 0 days.

(21) Appl. No.: 15/102,406

(22) PCT Filed: Dec. 12, 2014

(86) PCT No.: PCT/KR2014/012265
§ 371 (c)(1),
(2) Date: Jun. 7, 2016

(87) PCT Pub. No.: WO2015/088275
PCT Pub. Date: Jun. 18, 2015

(65) Prior Publication Data
US 2016/0317702 A1 Nov. 3, 2016

(30) Foreign Application Priority Data
Dec. 13, 2013 (KR) ........................ 10-2013-0155722
Jul. 15, 2014 (KR) ........................ 10-2014-0089173

(51) Int. Cl.
*A61L 24/04* (2006.01)
*A61L 26/00* (2006.01)
(Continued)

(52) U.S. Cl.
CPC ........... *A61L 24/08* (2013.01); *A61L 24/0015* (2013.01); *A61L 24/0031* (2013.01);
(Continued)

(58) Field of Classification Search
None
See application file for complete search history.

(56) References Cited

U.S. PATENT DOCUMENTS

| 6,806,260 | B1 | 10/2004 | Hirofumi et al. |
| 2005/0238702 | A1 | 10/2005 | Ishihara et al. |

(Continued)

FOREIGN PATENT DOCUMENTS

| EP | 2535041 A1 | 12/2012 |
| JP | 2006-347883 A | 12/2006 |

(Continued)

OTHER PUBLICATIONS

Hermanson, "Bioconjugate Techniques", Academic Press, 2013, pp. 1-1200 (pp. 201 and 205 are attached).*

(Continued)

*Primary Examiner* — Ernst V Arnold
*Assistant Examiner* — Kyung S Chang
(74) *Attorney, Agent, or Firm* — Clark & Elbing LLP; Susan M. Michaud

(57) ABSTRACT

The present invention provides a biodegradable medical adhesive or a sealant composition containing an oxidized glycosaminoglycan and a polyamine. The composition of the present invention exhibits improved effects in biodegradation, coating property, gelation time, hemostatic capacity, adhesive force, moisture absorptive capacity and the like, and thus can be applied to various medical uses in which a medical adhesive or sealant can be used, such as biotissue adhesion, filling, coating, adhesion prevention, wound covering, leakage prevention and hemostasis.

7 Claims, 12 Drawing Sheets

(51) Int. Cl.

| | |
|---|---|
| *A61L 27/52* | (2006.01) |
| *C08L 5/00* | (2006.01) |
| *C08L 71/00* | (2006.01) |
| *A61L 24/08* | (2006.01) |
| *A61L 27/20* | (2006.01) |
| *A61L 27/58* | (2006.01) |
| *A61L 24/00* | (2006.01) |
| *A61L 27/54* | (2006.01) |
| *A61L 24/10* | (2006.01) |
| *A61L 27/18* | (2006.01) |
| *A61L 27/22* | (2006.01) |
| *A61L 27/26* | (2006.01) |

(52) U.S. Cl.
CPC ......... *A61L 24/0042* (2013.01); *A61L 24/043* (2013.01); *A61L 24/046* (2013.01); *A61L 24/108* (2013.01); *A61L 26/008* (2013.01); *A61L 26/009* (2013.01); *A61L 26/0019* (2013.01); *A61L 26/0023* (2013.01); *A61L 26/0047* (2013.01); *A61L 26/0052* (2013.01); *A61L 26/0066* (2013.01); *A61L 27/18* (2013.01); *A61L 27/20* (2013.01); *A61L 27/227* (2013.01); *A61L 27/26* (2013.01); *A61L 27/52* (2013.01); *A61L 27/54* (2013.01); *A61L 27/58* (2013.01); *A61L 2300/418* (2013.01); *A61L 2300/604* (2013.01); *A61L 2400/04* (2013.01); *A61L 2430/34* (2013.01)

(56) References Cited

U.S. PATENT DOCUMENTS

| | | | | |
|---|---|---|---|---|
| 2008/0317818 A1* | 12/2008 | Griffith | ............... | A61K 9/0051 424/427 |
| 2010/0254906 A1* | 10/2010 | Denizot | ............... | A61K 51/065 424/9.1 |
| 2010/0272804 A1* | 10/2010 | Lu | ...................... | A61L 24/0031 424/484 |
| 2012/0245323 A1* | 9/2012 | Buffa | ................. | C08B 37/0072 530/322 |

FOREIGN PATENT DOCUMENTS

| | | | |
|---|---|---|---|
| JP | 2009-507110 A | 2/2009 | |
| JP | 2013-513671 A | 4/2013 | |
| KR | 10-2005-0045113 A | 5/2005 | |
| KR | 10-2007-0100230 A | 10/2007 | |
| KR | 10-2012-0089506 A | 8/2012 | |
| RU | 2006129942 A | 2/2008 | |
| WO | WO-96/02258 A1 | 2/1996 | |
| WO | WO-00/27889 A1 | 5/2000 | |
| WO | WO-2004/029137 A2 | 4/2004 | |
| WO | WO-2005/068645 A2 | 7/2005 | |
| WO | WO 2008067655 A1 * | 6/2008 | ............ A61L 27/20 |
| WO | WO-2009/132228 A1 | 10/2009 | |

OTHER PUBLICATIONS

International Search Report for PCT Application No. PCT/KR2014/012265, dated Mar. 26, 2015 (7 pages).

Extended European Search Report dated Jul. 13, 2017 for European Patent Application No. 14870365.5, Lee et al., "Biodegradable Medical Adhesive or Sealant Composition," filed Dec. 12, 2014 (12 pages).

Li et al., "Biodegradable and injectable in situ cross-linking chitosan-hyaluronic acid based hydrogels for postoperative adhesion prevention," Biomaterials. 35(12):3903-17 (2014).

Office Action dated Apr. 4, 2017 for Japanese Patent Application No. 2016-538741, Lee et al., "Biodegradable Medical Adhesive or Sealant Composition," filed Dec. 12, 2014 (8 pages).

Office Action dated Sep. 6, 2017 for Canadian Patent Application No. 2933271, Lee et al., "Biodegradable Medical Adhesive or Sealant Composition," filed Dec. 12, 2014 (6 pages).

Chapter 2: Faerie Soda. Soda Green Coffee Giberty for Weight Loss, 67 (2014). Saint Petersburg, Piter (4 pages).

Ya, Non-metallic Materials. Combating corrosion in chemical and petroleum industries, Klinova ed., Mechanical Engineering, p. 119 (1968) (4 pages).

Office Action dated Dec. 15, 2017 for Russian Application No. 2016128376, Lee et al., "Biodegradable Medical Adhesive or Sealant Composition," filed Dec. 12, 2014 (19 pages).

* cited by examiner

Fig 4

| | No. | | | Gelation time (s) |
|---|---|---|---|---|
| | 1 | 2 | 3 | |
| LYDEX | | | | 10 ↑ |
| CHO-HA 150 | | | | 2.8 |
| CHO-HA 1400 | | | | 3.1 |

BIODEGRADABLE MEDICAL ADHESIVE OR SEALANT COMPOSITION

TECHNICAL FIELD

The present invention relates to a biodegradable medical adhesive or sealant composition containing an oxidized glycosaminoglycan having a formyl group and a polyamine.

BACKGROUND ART

Bio-adhesives or sealants are used to suture or coat tissues at surgery, or are used as a bleeding-preventing agent (hemostasis), a body fluid and blood blocking agent, or the like. Bio-adhesives or sealants are required to have biocompatibility due to a contact with the skin, to have no toxicity and risk in the body, to be biodegradable, and not to obstruct the healing of the body.

Medical adhesive materials, which are currently practically used, include cyanoacrylates, fibrin glues, gelatin glues, and polyurethanes. A medical tissue adhesive of octyl cyanoacrylate, which was commercially available under the trade name "Dermabond" from Closure Medical Corp., USA, was approved for marketing by the EC in August, 1997 and approved for use by the US FDA in 1998. However, cyanoacrylate-based adhesives may obstruct wound healing since the solid products thereof are inflexible and hard, and are easy to become foreign materials since they are difficult to degrade in the body and are thus encapsulated. Moreover, fibrin glues may cause the separation of generated fibrin clots from tissues since the adhesive strength thereof is significantly low, and may cause a concern about viral infection since they are blood materials.

In addition to the foregoing medical adhesives, Korean Patent Publication No. 10-2009-0083484 discloses a two-component adhesive for medical use (Product name: LYDEX) containing an aldehyded dextran powder and an ε-poly-L-lysine powder, the adhesive being prepared by freeze-drying and then mechanical pulverization. The two-component adhesive is characterized by being a powder type medical adhesive, but it requires a relatively long time for gel degradation and does not obtain a desirable moisture absorption effect. Therefore, there is an increasing demand for novel medical adhesives having improved features in view of degradation time, adhesive strength, and moisture absorption power.

Throughout the entire specification, many papers and patent documents are referenced and their citations are represented. The disclosure of the cited papers and patent documents are entirely incorporated by reference into the present specification and the level of the technical field within which the present invention falls, and the details of the present invention are explained more clearly.

DETAILED DESCRIPTION OF THE INVENTION

Technical Problem

The present inventors have endeavored to research and develop biodegradable medical adhesives and sealants that: can perform sufficient adhesion, covering, and hemostasis on sites in the body in which the body fluid and blood are present; can absorb a lot of moisture compared with other biodegradable polymers; and is self-degradable in the body. As a result, the present inventors have verified that effective adhesion, filling, coating, anti-adhesion, wound covering, and hemostasis can be performed on biological tissues by using a glycosaminoglycan, which is oxidized by the introduction of a formyl group, together with a polyamine, and thus have completed the present invention.

An aspect of the present invention is to provide a medical adhesive or sealant (or a medical adhesive or sealant composition).

Another aspect of the present invention is to provide a method for performing adhesion, filling, coating, anti-adhesion, wound covering, or hemostasis on biological tissues.

Other purposes and advantages of the present disclosure will become more obvious with the following detailed description of the invention, claims, and drawings.

Technical Solution

In accordance with an aspect of the present invention, there is provided a biodegradable medical adhesive or sealant (or medical adhesive or sealant composition), including:

(a) a first component containing an oxidized glycosaminoglycan obtained by oxidation through the introduction of a formyl group; and (b) a second component containing a polyamine having two or more amino groups, the pH of the second component in an aqueous solution phase being 8.5-11.0.

In accordance with another aspect of the present invention, there is provided a biodegradable medical adhesive or sealant (or medical adhesive or sealant composition), including:

(a) a first component containing an oxidized glycosaminoglycan obtained by oxidation through the introduction of a formyl group; and (b) a second component containing a polyamine having two or more amino groups, the pH of the second component in an aqueous solution phase being 8.5-11.0, wherein, when the first and second components are mixed, the molar ratio of the formyl group/the amino group is 0.1-500.

In accordance with still another aspect of the present invention, there is provided a method for performing adhesion, filling, coating, anti-adhesion, wound covering, and hemostasis, on biological tissues, the method a step of applying the biodegradable medical adhesive or sealant (or medical adhesive or sealant composition) of claim 1 to biological tissues in need of adhesion, filling, coating, anti-adhesion, wound covering, and hemostasis.

The present inventors have endeavored to research and develop biodegradable medical adhesives and sealants that: can perform sufficient adhesion, covering, and hemostasis on sites in the body in which the body fluid and blood are present; can absorb a lot of moisture compared with other biodegradable polymers; and is self-degradable in the body. As a result, the present inventors have verified that effective adhesion, filling, coating, anti-adhesion, wound covering, and hemostasis can be performed on biological tissues by using a glycosaminoglycan, which is oxidized by the introduction of a formyl group, together with a polyamine.

Herein, the medical adhesive or sealant and the composition thereof are inter-exchangeably used.

As confirmed in the examples below, the composition of the present invention showed improved effects in the gel formation time, adhesive strength, and moisture absorption power, compared with an existing two-component medical adhesive (LYDEX) (see tables 5 to 7), and showed a superior hemostatic effect compared with an existing hemostatic agent (Arista™AH) (see FIG. 12). These results indicated that the composition of the present invention, which contains a combination of the first component and the second component, exhibited excellent physical properties in view of medical uses, such as adhesion, filling, coating, anti-adhesion, wound covering, and hemostasis with respect to biological tissues, and thus the composition of the present invention can be used for the medical uses thereof.

The composition of the present invention contains an oxidized glycosaminoglycan as the first component. The term "oxidized glycosaminoglycan" means that a glycosaminoglycan has been oxidized by introducing a formyl group (—CHO) thereinto. The glycosaminoglycan, which is a polysaccharide having a disaccharide repeating structure, including hexosamine, is differentiated from a glucan composed of monosaccharides linked by O-glycosidic bonds.

The introduction of such a formyl group may be conducted by periodic acid oxidation. For example, a glycosaminoglycan may be oxidized with periodic acid or a periodic acid salt to obtain an oxidized glycosaminoglycan, into which an appropriate number (e.g., 0.01-0.95) of formyl groups per anhydrous glucose unit (sugar residue) are introduced.

According to an embodiment of the present invention, the degree of oxidation of the oxidized glycosaminoglycan is calculated by the following equation:

$$\text{Degree of oxidation (\%)} = \frac{\text{number of moles of CHO}}{\text{number of mols of oxidized glycosaminoglycan}} \times 100,$$

and has a value of 10-99.5%. The oxidized glycosaminoglycan having such a degree of oxidation, when used in combination with the second component, may promptly absorb the blood and body fluid in the body to perform the gelation of the blood and body fluid in a quick time.

The degree of oxidation of the oxidized glycosaminoglycan is 10-60% for a specific embodiment, 10-55% for another specific embodiment, 10-50% for still another specific embodiment, 10-45% for still another specific embodiment, and 10-40% for still another specific embodiment. For example, the first component contains at least one type of oxidized glycosaminoglycan, and in cases where this type of oxidized glycosaminoglycan is oxidized hyaluronic acid, the degree of oxidation of the oxidized hyaluronic acid may be 10-20%.

The degree of oxidation of the glycosaminoglycan may be measured by NaOH titration. For example, a 0.25 mol/l hydroxylamine hydrochloride solution is prepared by mixing 17.5 g of hydroxylamine hydrochloride and 6 ml of 0.05% methyl orange in 994 ml of distilled water, and titrated to pH 4. Then, 0.1 g of an oxidized glycosaminoglycan is dissolved in 25 ml of the solution, and titrated with 0.1 mol/l sodium hydroxide to pH 4, and then the degree of oxidation (%) thereof is calculated by the following equation:

$$\text{Degree of oxidation (\%)} = \frac{\text{concentration of sodium hydroxide} \times \text{volume of sodium hydroxide} \times 10^{-3}}{\frac{\text{weight of oxidized glycosaminoglycan}}{\text{amount of glycosaminoglycan repeating unit}}} \times 100.$$

According to an embodiment of the present invention, the oxidized glycosaminoglycan has 0.01 to 0.95 formyl groups per anhydrous glucose unit (sugar residue).

According to an embodiment of the present invention, the oxidized glycosaminoglycan is selected from the group consisting of oxidized hyaluronic acid, oxidized chondroitin sulfate, oxidized chondroitin, oxidized dermatan sulfate, oxidized heparan sulfate, oxidized heparin, and oxidized keratan sulfate.

According to the present invention, the gelation ability, duration of the gelled state, and gel elasticity of the adhesive/sealant composition may be controlled by using a glycosaminoglycan with a particular molecular weight.

According to an embodiment of the present invention, the glycosaminoglycan used to obtain the oxidized glycosaminoglycan has a molecular weight of 1,000 to 5,000,000. For example, the glycosaminoglycan used to obtain the oxidized glycosaminoglycan may have a molecular weight of 10,000 to 4,000,000, 50,000 to 3,500,000, 100,000 to 3,500,000, 100,000 to 3,000,000, 100,000 to 2,500,000, 100,000 to 2,000,000, or 100,000 to 1,600,000.

According to an embodiment of the present invention, the first component contains oxidized hyaluronic acid having a molecular weight of 100,000 to 2,000,000. According to an embodiment, the molecular weight of oxidized hyaluronic acid is 100,000 to 1,600,000.

According to an embodiment of the present invention, the first component contains two or more types of oxidized glycosaminoglycans.

According to an embodiment of the present invention, the weight ratio of these types of oxidized glycosaminoglycans is 1:0.5-5. The weight ratio of the oxidized glycosaminoglycans is 1:0.5-4 for a specific embodiment, 1:0.5-3.5 for another specific embodiment, 1:0.5-3 for still another specific embodiment, 1:0.5-2.5 for still another specific embodiment, 1:0.5-2 for still another specific embodiment, and 1:0.5-1.5 for still another specific embodiment.

According to an embodiment of the present invention, the two or more types of oxidized glycosaminoglycans are oxidized hyaluronic acid and oxidized chondroitin sulfate. The weight ratio of the oxidized hyaluronic acid and the oxidized chondroitin sulfate may be 1:0.5-5, 1:0.5-4, 1:0.5-3.5, 1:0.5-3, 1:0.5-2.5, 1:0.5-2, 1:0.5-1.5, or 1:0.8-1.2.

According to an embodiment of the present invention, the degree of oxidation of the oxidized hyaluronic acid is 10-40%. The degree of the oxidized hyaluronic acid is 12-40% for a specific embodiment, 12-38% for another specific embodiment, and 13-37% for still another specific embodiment.

According to an embodiment of the present invention, the degree of oxidation of the oxidized chondroitin sulfate is 10-55%. The degree of the oxidized chondroitin sulfate is 10-50% for a specific embodiment, 10-45% for another specific embodiment, 10-40% for still another specific embodiment, and 10-35% for still another specific embodiment.

According to an embodiment, the first component is in a powder state, a liquid state, or a solid state (e.g., pellet form). For example, the first component in a powder state may be obtained by drying (e.g., spray drying, freeze-drying, etc.) an oxidized glycosaminoglycan-containing solution, followed by pulverization (e.g., mechanical pulverization).

The composition of the present invention further contains, in addition to the first component, a second component containing a polyamine having two or more amino groups, as an active ingredient. The second component exhibits a pH of 8.5-11.0 in an aqueous solution phase. As confirmed in the following examples, in cases where the pH of the second component in an aqueous solution phase is 8.5-11.0, the gelation may occur within seconds (see FIG. 7).

According to a specific embodiment, the second component shows a pH of 9.0-11.0 in an aqueous solution phase.

According to an embodiment, the polyamine may further have a secondary and/or tertiary amino group.

According to an embodiment, the polyamine containing the second component is in a powder state, a liquid state, or a solid state (e.g., pellet form). For example, the second component in a powder state may be obtained by drying a polyamine-containing solution, followed by pulverization. Here, the polyamine-containing solution may further contain a pH adjuster such that the pH range of the second component in an aqueous solution phase is 8.5-11.0. Examples of the pH adjuster may be monovalent or multi-valent carbonic acid compounds, such as acetic acid, citric acid, succinic acid, glutaric acid, malic acid, fumaric acid, and maleic acid, or anhydrides thereof.

According to an embodiment of the present invention, the polyamine is selected from the group consisting of polylysine, chitosan, albumin, putrescine, cadaverine, spermidine, spermine, protamine, and polyethylenimine (PEI).

According to an embodiment of the present invention, the polyamine has a molecular weight of 100 or more. For example, the molecular weight of the polyamine may be 1,000 to 200,000.

According to an embodiment of the present invention, the polyamine is poly-L-lysine. The poly-L-lysine may be ε-poly-L-lysine that is produced using microorganisms (e.g., *Streptomyces albulus*) or an enzyme.

According to an embodiment of the present invention, the second component may further contain, in addition to the polyamine, a pH adjuster.

According to an embodiment of the present invention, the composition of the present invention may further contain a drug. For example, the drug may be contained in the second component. The drug may have at least one amine group, and examples of the drug may include anthracycline-based drugs, gemcitabine, vancomycin, polymyxin, methotrexate, protein drugs, and peptide drugs. In this case, when the first component and the second component are gelated, the amine group of the drug also reacts with the formyl group of the first component, so that the three components may form a gel together. As the formed gel is disrupted, the drug is slowly released to exhibit pharmaceutical activity.

According to an embodiment of the present invention, the composition of the present invention may be formulated into several forms, and may contain, for example, a combination of a first component in a powder state, a liquid state, or a solid state (e.g., pellet form) and a second component in a powder state, a liquid state, or a solid state.

According to an embodiment of the present invention, the composition of the present invention contains a first component and a second component at a weight ratio of 0.5-10:1.

The first component and the second component may be contained at a weight ratio of 0.5-8:1 for a specific embodiment, at a weight ratio of 0.5-6:1 for another specific embodiment, at a weight ratio of 0.5-4:1 for still another specific embodiment, at a weight ratio of 0.5-3:1 for still another specific embodiment, at a weight ratio of 0.5-2:1 for still another specific embodiment, at a weight ratio of 0.5-1.5:1 for still another specific embodiment, at a weight ratio of 0.8-1.5:1 for still another specific embodiment, and at a weight ratio of 0.8-1.2:1 for still another specific embodiment.

According to the present invention, the gel formation time or the degradation time of the formed gel can be controlled by adjusting the ratio of the formyl group of the first component and the amino group of the second component.

According to an embodiment of the present invention, the molar ratio of the formyl group/the amino group is 0.1-500 in cases where the first component is mixed with the second component.

In cases where the first component is mixed with the second component the molar ratio of the formyl group/the amino group is 1-400 for a specific embodiment, 1-350 for another specific embodiment, 1-300 for still another specific embodiment, and 10-300 for still another specific embodiment.

The first component and the second component may be coated on an adherend (in vivo or in vitro skin surface) simultaneously or sequentially, for a medical effect (medical use). Here, in some cases, a saline solution or distilled water may be sprayed for the gelation of the first component and the second component.

According to an embodiment of the present invention, the medical use is selected from the group consisting of adhesion, filling, coating, anti-adhesion, wound covering, and hemostasis, with respect to biological tissues.

The composition of the present invention is provided in a form in which the first component and the second component are contained in the same container or are separately contained in separate containers.

Advantageous Effects

Features and advantages of the present invention are summarized as follows:

(i) The present invention provides a biodegradable medical adhesive or sealant composition containing an oxidized glycosaminoglycan and a polyamine.

(ii) The composition of the present invention exhibits improved effects in biodegradability, coatability, gelation time, hemostatic ability, adhesive strength, and moisture absorption power.

(iii) The composition of the present invention may be utilized for various medical uses for which medical adhesives or sealants are usable, such as adhesion, filling, coating, anti-adhesion, wound covering, anti-leakage, and hemostasis, with respect to biological tissues.

BRIEF DESCRIPTION OF THE DRAWINGS

FIG. 4 shows images illustrating the comparison of gelation time between adhesive and sealant compositions of the present invention and an existing adhesive composition (LYDEX).

FIGS. 8 to 11 illustrate comparative test results between an adhesive and sealant composition of the present invention and an existing hemostatic agent (Arista™AH) on a hepatolobectomy model, a nephrectomy model, a gastric mucosectomy model, and a vascular hemorrhage model.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1: Preparation of Medical Adhesive (1)

(1) Preparation of Oxidized Hyaluronic Acid (CHO-HA; First Component)

1 g or 3 g of hyaluronic acid (HA) with a molecular weight of 7 kDa, 150 kDa, 1400 kDa, or 3000 kDa was dissolved in 150 ml of sodium periodate ($NaIO_4$) in water. Here, the concentration and reaction conditions of sodium periodate was varied as shown in tables 1 to 4 to make varying degrees of oxidation (degree of substitution (DS), %). A reaction flask was allowed to react at 15-70° C. for 3-48 h. The reaction material was dialyzed with distilled water for 24 h using a dialysis membrane with a molecular weight cut-off of 1-100 kDa. Here, the obtained oxidized hyaluronic acid was freeze-dried for 4 days, followed by pulverization, and then passed through a 500 μm-sized mesh to give oxidized hyaluronic acid with a diameter of about 500 μm or smaller.

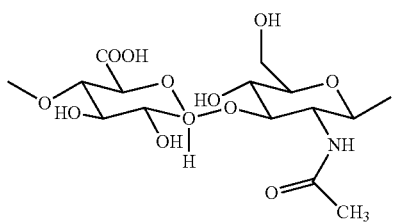

HA

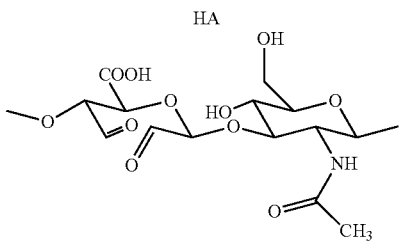

Oxidized hyaluronic acid CHO-HA

Figure 1:
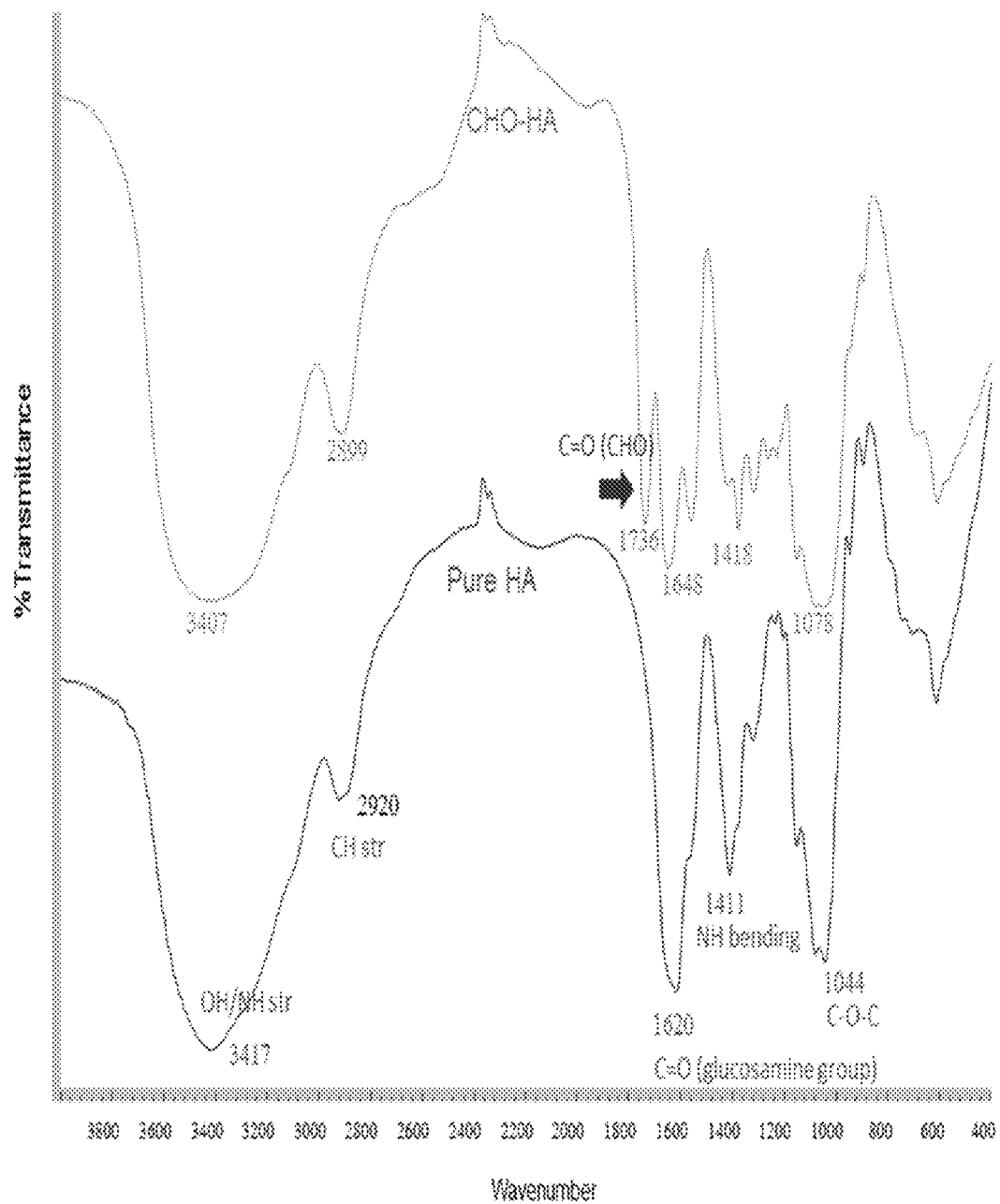
FIG. 1 illustrates analysis results of oxidized hyaluronic acid using an FT-IR spectrometer.

As a result of analysis of the oxidized hyaluronic acid using an FT-IR spectrometer (Cary 640, Agilent Technologies, USA), the substituents were confirmed at 4000-400 $cm^{-1}$ (resolution 4 $cm^{-1}$) (FIG. 1).

In order to investigate the degree of oxidation of hyaluronic acid, 17.5 g of hydroxylamine hydrochloride and 6 ml of 0.05% methyl orange were mixed in 994 ml of distilled water to prepare a 0.25 M hydroxylamine hydrochloride solution, which was then titrated to pH 4. 0.1 g of oxidized hyaluronic acid was dissolved in 25 ml of the solution, and then titrated to pH 4 with 0.1 mM sodium hydroxide. The degree of oxidation (%) was calculated by the following equation, and the results are shown in tables 1 to 4.

$$\text{Degree of oxidation (\%)} = \frac{\text{number moles of CHO}}{\text{number of mols of oxidized } HA} \times 100 = \frac{\text{concentration of sodium hydroxide} \times \text{volume of sodium hydroxide} \times 10^{-3}}{\frac{\text{weight of oxidized hyaluronic acid}}{\text{amount of hyaluronic acid repeating unit}}} \times 100$$

Equation 1

TABLE 1

| HA M.W. (kDa) | DS (%) | HA weight (g) | Oxidant concentration (mM) | Reaction temperature (° C.) | Reaction time (h) |
|---|---|---|---|---|---|
| 7 | 67.4 | 3.1 | 15.8 | 40 | 24 |
|   | 75.9 | 3.1 | 15.7 | 40 | 24 |
|   | 79.3 | 1.0 | 15.8 | 40 | 24 |

TABLE 2

| HA M.W. (kDa) | DS (%) | HA weight (g) | Oxidant concentration (mM) | Reaction temperature (° C.) | Reaction time (h) |
|---|---|---|---|---|---|
| 150 | 4.0 | 1.0 | 2.6 | RT. | 24 |
|   | 5.7 | 1.0 | 2.6 | 40 | 6 |
|   | 7.2 | 1.1 | 2.6 | RT. | 6 |
|   | 11.6 | 1.0 | 2.6 | 40 | 24 |
|   | 16.8 | 3.1 | 7.9 | 40 | 24 |
|   | 17.2 | 1.0 | 5.3 | RT. | 6 |
|   | 19.5 | 1.0 | 7.8 | RT. | 6 |
|   | 36.5 | 3.0 | 15.7 | 40 | 24 |
|   | 37.4 | 3.1 | 15.8 | 40 | 24 |
|   | 48.4 | 3.1 | 23.4 | 40 | 24 |
|   | 82.2 | 1.0 | 15.7 | 40 | 24 |

TABLE 3

| HA M.W. (kDa) | DS (%) | HA weight (g) | Oxidant concentration (mM) | Reaction temperature (° C.) | Reaction time (h) |
|---|---|---|---|---|---|
| 1400 | 2.2 | 1.1 | 2.5 | RT. | 3 |
|   | 8.3 | 1.1 | 2.8 | 40 | 3 |
|   | 3.9 | 1.0 | 2.6 | RT. | 24 |
|   | 7.6 | 1.1 | 2.6 | RT. | 6 |
|   | 9.2 | 1.0 | 3.8 | RT. | 6 |
|   | 9.7 | 1.0 | 2.7 | 40 | 6 |
|   | 9.9 | 1.0 | 5.3 | RT. | 6 |
|   | 11.3 | 1.0 | 3.8 | RT. | 6 |
|   | 14.0 | 1.0 | 5.2 | RT. | 6 |
|   | 14.3 | 1.0 | 2.6 | 40 | 24 |
|   | 14.8 | 3.1 | 8.0 | 40 | 6 |
|   | 15.4 | 1.0 | 7.8 | RT. | 6 |
|   | 16.5 | 1.0 | 3.8 | RT. | 6 |
|   | 17.4 | 3.1 | 7.9 | 40 | 24 |

TABLE 3-continued

| HA M.W. (kDa) | DS (%) | HA weight (g) | Oxidant concentration (mM) | Reaction temperature (° C.) | Reaction time (h) |
|---|---|---|---|---|---|
| | 17.7 | 1.0 | 5.3 | RT. | 6 |
| | 18.0 | 1.0 | 9.6 | RT. | 6 |
| | 19.5 | 1.0 | 11.1 | RT. | 6 |
| | 21.0 | 1.0 | 11.0 | RT. | 6 |
| | 21.6 | 1.0 | 12.7 | RT. | 6 |
| | 21.9 | 1.0 | 9.4 | RT. | 6 |
| | 22.8 | 1.0 | 7.8 | RT. | 6 |
| | 23.2 | 1.1 | 7.9 | RT. | 6 |
| | 23.6 | 1.0 | 12.5 | RT. | 6 |
| | 24.7 | 1.0 | 11.1 | RT. | 6 |
| | 27.0 | 1.0 | 9.5 | RT. | 6 |
| | 30.9 | 1.0 | 12.7 | RT. | 6 |
| | 40.8 | 3.1 | 15.8 | 40 | 24 |
| | 47.7 | 3.1 | 23.5 | 40 | 24 |
| | 82.6 | 1.1 | 15.7 | 40 | 24 |

TABLE 4

| HA M.W. (kDa) | DS (%) | HA weight (g) | Oxidant concentration (mM) | Reaction temperature (° C.) | Reaction time (h) |
|---|---|---|---|---|---|
| 3000 | 4.4 | 1.0 | 2.6 | RT. | 24 |
| | 4.6 | 1.1 | 2.6 | RT. | 6 |
| | 4.7 | 1.1 | 2.5 | 40 | 6 |
| | 19.8 | 3.0 | 7.9 | 40 | 24 |
| | 23.3 | 1.1 | 2.6 | 40 | 24 |
| | 43.4 | 3.0 | 15.9 | 40 | 24 |
| | 82.2 | 1.1 | 15.7 | 40 | 24 |

(2) Second Component Having Two or More Amino Groups

Out of various amino group-containing polyamines, chitosan, protamine, PEI, polylysine, spermine, spermidine, and albumin were typically used as the second component. The powders, which were obtained by adjusting 5 wt % or more of polyamine solutions to pH 8.5, 9.0, 9.5, and 10 using pH adjusters (acid, acidic salt, base, basic salt), and then freeze-drying the solutions in the same manner as in the oxidized hyaluronic acid/oxidized chondroitin sulfate, was used.

Figure 2:
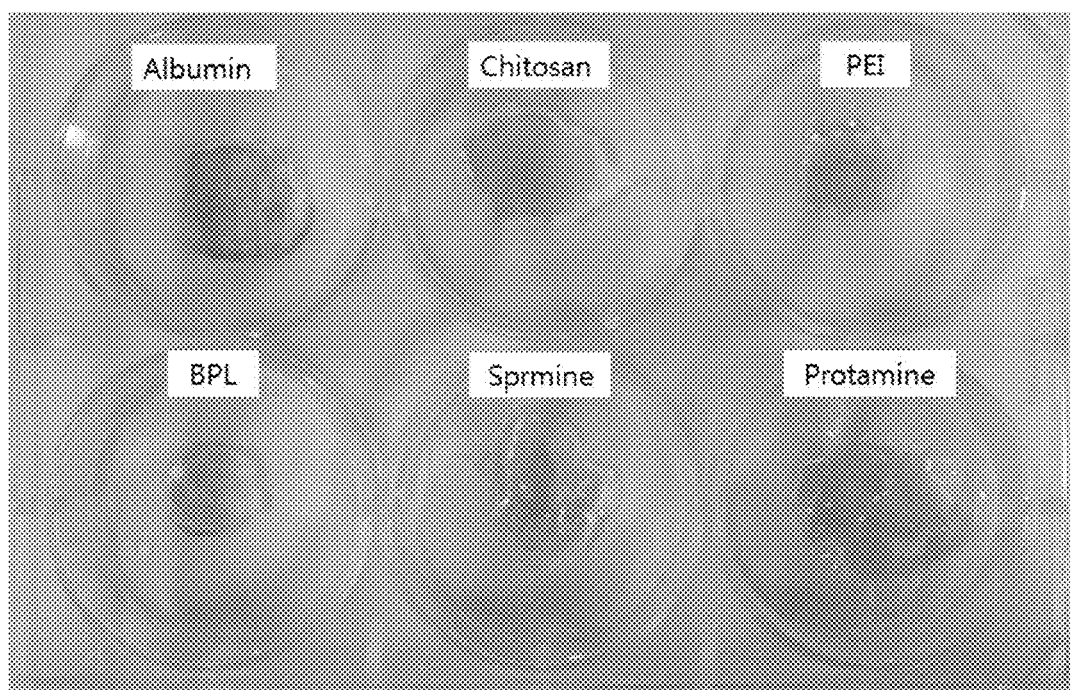
FIG. 2 shows an image illustrating the gelation state and gelation time of mixtures that use a second component having an amino group.

The gelation degree and gelation time of the listed amino group-containing polyamines were evaluated. As a result, albumin, basic polylysine (BPL), and PEI were excellent in view of the gelation rate and gel safety (FIG. 2). Of these, BPL was used for the following tests.

Example 2: Evaluation of Physical Properties (1) Evaluation of Gelation

The first and second components obtained in example 1 were mixed at different weight ratios (1:1, 2:1, 4:1, 8:1). The degree of gelation of the mixed components was confirmed by sprinkling water.

Figure 3:
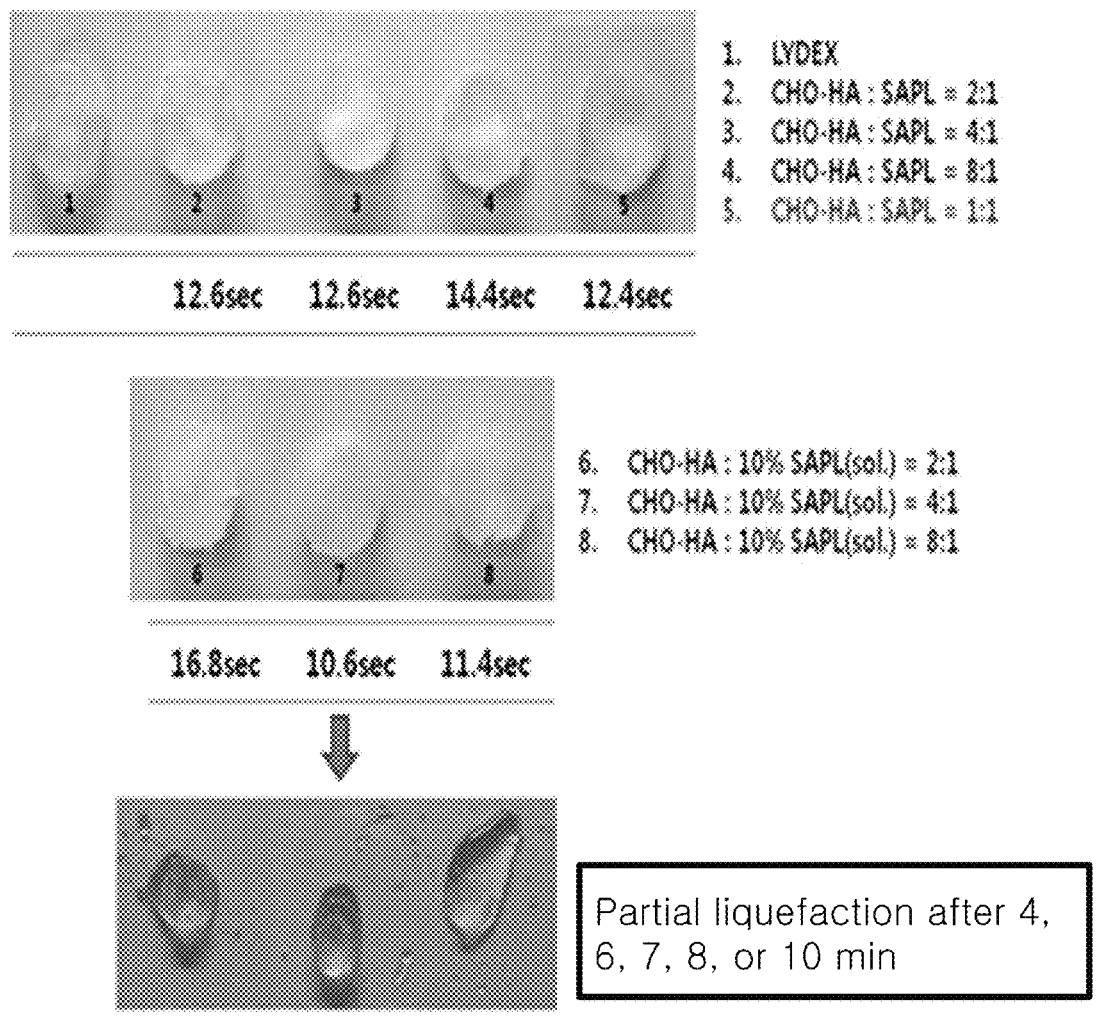
FIG. 3 shows images illustrating gelation evaluation results of mixtures of a first component and a second component mixed at different weight ratios.

As a result, the 8:1 mixture of the first component and the second component was partially changed into a liquid after 10 min, and the 2:1 mixture and the 4:1 mixture had relatively low gel elasticity compared with the 1:1 mixture (FIG. 3). In addition, the mixture preparation using a hyaluronic acid with a molecular weight of 3,000 kDa was gelated, but less elastic. As for hyaluronic acid with a molecular weight of 150 kDa and 1,400 kDa, the mixture preparation was gelated regardless of the degree of substitution, but when the degree of substitution was around 10% (10-19%), the mixtures showed a shorter gelation time and excellent elasticity.

Based on the above results, the first component (oxidized hyaluronic acid having a degree of substitution of 10%, obtained by introducing an aldehyde group into hyaluronic acid with a molecular weight of 150 kDa or 1,400 kDa) and the second component were mixed at a weight ratio of 1:1, and this mixture was used for the following tests.

(2) Evaluation of Gelation Time

The components mixed in a 2 ml tube were small divided into 30 mg, which was then collected in a tube cap. 120 µl of water was sprinkled thereon within 1 s, and then the gelation time was measured. LYDEX consumed 10 s or more in obtaining a solidified gel, in spite of employing a smaller amount (80 µl) compared with the hyaluronic acid mixture preparation. On the other hand, the oxidized hyaluronic acid mixture preparation showed a short gelation time of within 2-3 s (FIG. 4 and table 5).

TABLE 5

| | Gelation time (s) | |
|---|---|---|
| Sample | Mean | SD |
| LYDEX | 10 | 0.00 |
| CHO-HA 150 kDa | 2.87 | 0.62 |
| CHO-HA 1,400 kDa | 2.95 | 0.58 |

(3) Evaluation on Adhesive Strength

Figure 5:
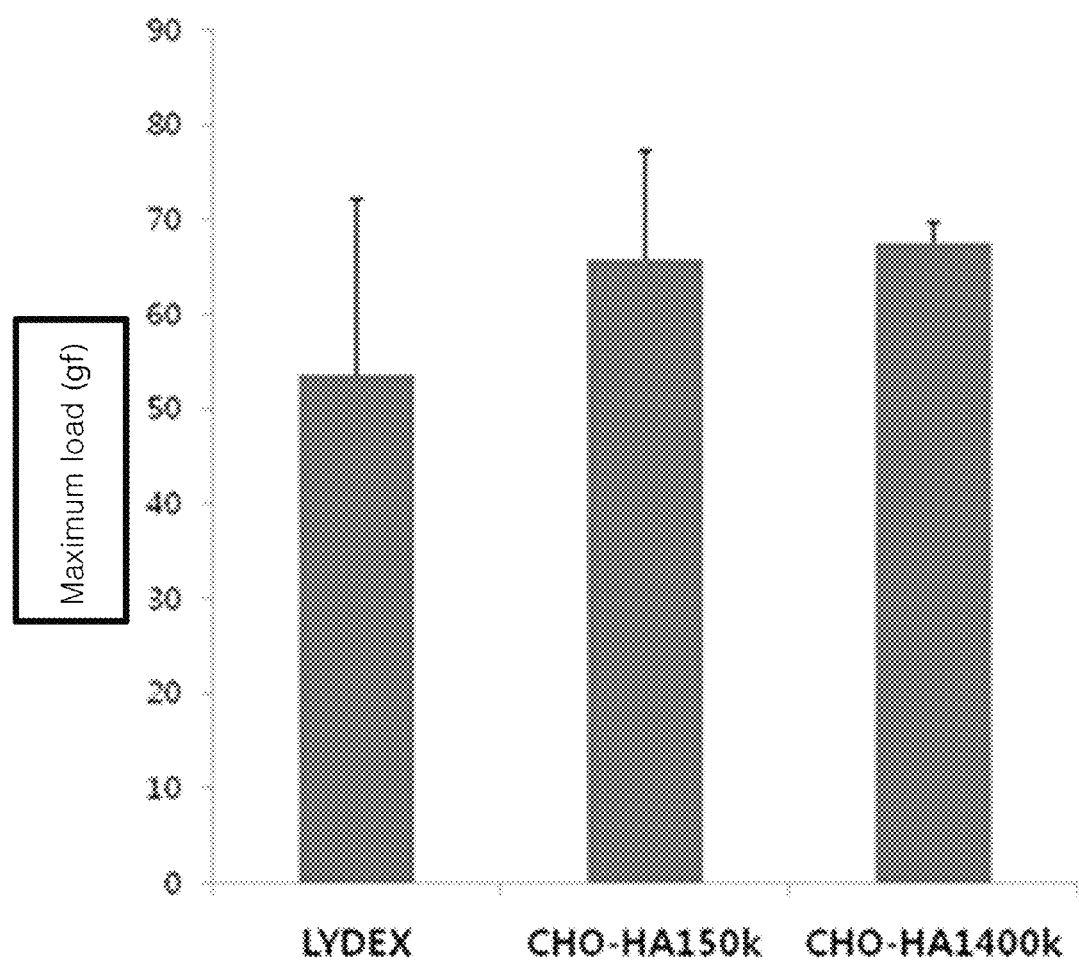
FIG. 5 shows a graph illustrating the comparison of adhesive strength between adhesive and sealant compositions of the present invention and an existing adhesive composition (LYDEX).

800 µl of water was sprinkled on 100 mg of the mixed components, and then the adhesive strength was measured using a Texture Analyzer. As a result, LYDEX showed a mean adhesive strength of about 53.6 gf in spited of employing a smaller amount (500 µl) compared with the oxidized hyaluronic acid mixture preparation. On the other hand, the oxidized hyaluronic acid mixture preparations were measured to have the mean adhesive strength values of 65.9 gf and 67.5 gf, respectively (FIG. 5 and table 6).

TABLE 6

| | Adhesive strength (gf) | |
|---|---|---|
| Sample | Mean | SD |
| LYDEX | 53.60 | 18.58 |
| CHO-HA 150 kDa | 65.86 | 11.32 |
| CHO-HA 1,400 kDa | 67.51 | 2.22 |

(4) Evaluation of Absorption Power

Absorption power was evaluated for LYDEX, and CHO-HA 150 kDa (DS 10%) and CHO-HA 1,400 kDa (DS 10%) mixed with the second component. 30 mg of each sample was placed on a petri dish (Φ60), and weighed. Distilled water, which was previously warmed at 37° C., was added to the sample, and here, the weight of the distilled water was 30 times (30 g) the weight of the sample, considering the absorption power of the product. The resultant material was left in a thermostat at 37° C. for 30 min, and then the petri dish was overturned for 30 s to measure the weight. The absorption power was calculated by the following equation.

$$\text{Absorption power (\%)} = \frac{\text{Sample weight (mg) after 30 min} - \text{Initial weight (mg)}}{\text{Initial weight (mg)}} \times 100 \qquad \text{Equation 2}$$

As a result, it was verified that the absorption power of the oxidized hyaluronic acid mixture preparation (CHO-HA 1,400 kDa) was excellent by about 5-fold compared with an existing LYDEX formulation (table 7).

TABLE 7

| Sample | Absorption power (%) | |
|---|---|---|
| | Mean | SD |
| LYDEX | 4.2 | 0.1 |
| CHO-HA 150 kDa | 17.6 | 3.5 |
| CHO-HA 1,400 kDa | 19.9 | 0.4 |

Example 3: In Vivo Evaluation (1) Animals

Three male rabbits (New Zealand White; Orient Bio, Seongnam, Korea) weighing 2-3 kg were used for a test. All animal breeding and test procedures were conducted according to the guidelines of the Experimental Animal Research Committee of Inha University.

(2) Gastric Hemorrhage Inducing Animal Model

The rabbit mucosectomy-induced gastric hemorrhage model was constructed as follows. Rabbits were fasted for 24 h prior to the surgery, then anesthetized with an intramuscular injection of a mixture of ketamine (4.2 mg/kg) and xylazine (11.7 mg/kg). The upper part of the belly was incised to expose the stomach, and a 5-7 cm incision was made along the greater curvature. 200 µl of isotonic saline was injected into the submucosal layer of the stomach, and then the swollen gastric mucosa was resected using surgery scissors. The diameter of the resected part was around 7-10 mm.

(3) Mucosal Adhesive Ability and Hemostatic Ability

Figure 6:
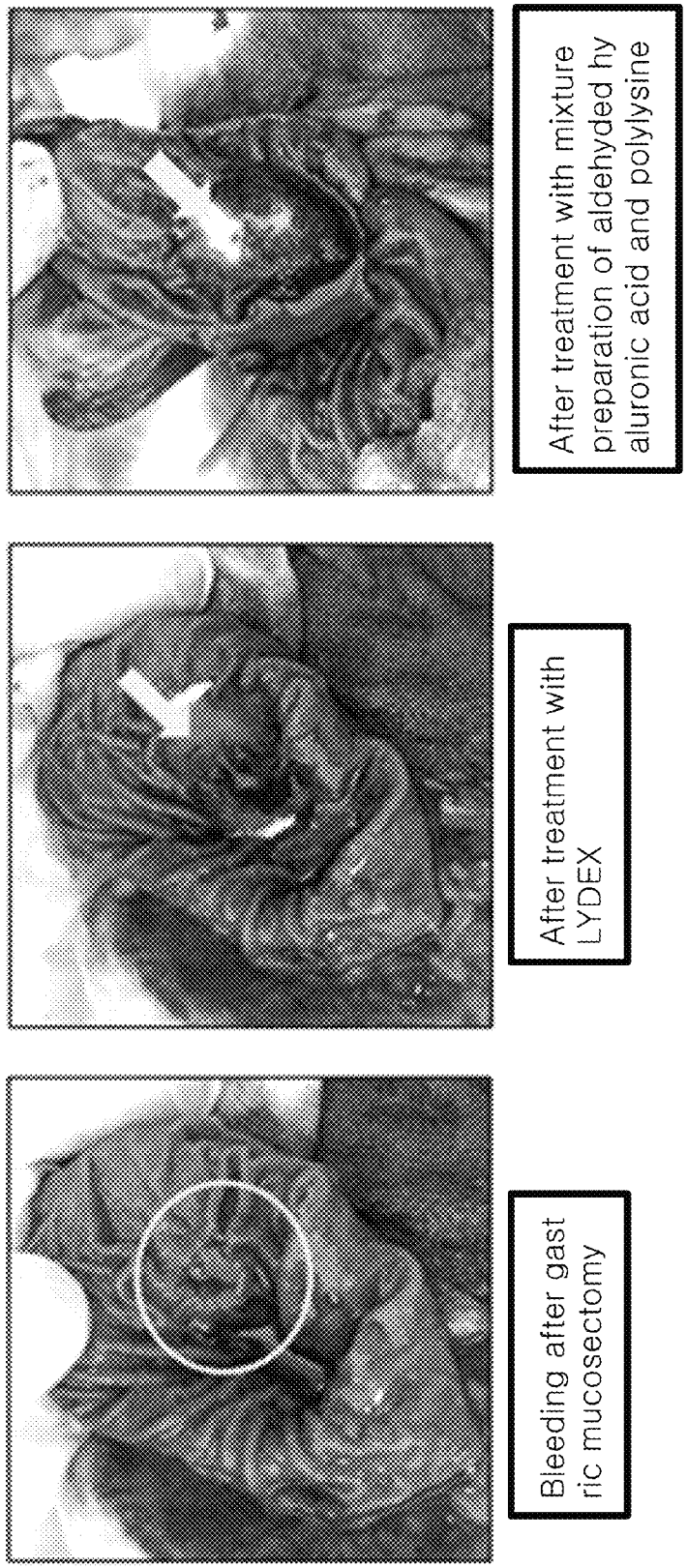
FIG. 6 shows images illustrating results (of mucosal adhesive ability and hemostatic ability) when a bleeding site after gastric mucosectomy is coated with the adhesive and sealant composition of the present invention or an existing adhesive composition (LYDEX).

Approximately 0.5 g of a mixture preparation (mixture of the first component and the second component at a weight ratio of 1:1) was coated on the resected bleeding gastric mucosa of the rabbit, which is bleeding. As a result, as shown in FIG. 6, the gelation of the mixture preparation occurred through the reaction of the mixture preparation and the blood immediately after the mixture preparation was coated, and the bleeding time was shortened compared with the non-treatment group. In addition, the mucosal adhesive ability of the composition of the present invention was confirmed (FIG. 6).

Example 4: Preparation of Medical Adhesive (2)

(1) Preparation of Oxidized Hyaluronic Acid and Oxidized Chondroitin Sulfate (First Component)

3 g of hyaluronic acid (Shandong Bloomage Freda Biopharm Co., Ltd) with a molecular weight of 1,400 kDa was dissolved in 150 ml of distilled water. Then, as shown in table 1, sodium periodate (molecular weight: 213.89) was added, and a reaction flask was allowed to react with stirring at 40° C. for 24 h. Then, the solution after the reaction was dialyzed with distilled water for 48 h (using a dialysis membrane with a molecular weight cut-off of 12000-14000), and then freeze-dried.

3 g of chondroitin sulfate (Yantai Dongcheng Biochemical Co., Ltd) with a molecular weight of 5,000-50,000 was dissolved in 15 ml of distilled water. Then, as shown in table 2, sodium periodate (molecular weight: 213.89) was added, and the mixture was allowed to react with stirring at room temperature for 18 h. Then, the solution after the reaction was dialyzed with distilled water for 48 h (using a dialysis membrane with a molecular weight cut-off of 12000-14000), and then freeze-dried.

In the following test, the oxidized hyaluronic acid and the oxidized chondroitin sulfate were used as the first component.

The degrees of substitution (degrees of oxidation) of hyaluronic acid and chondroitin sulfate were confirmed through NaOH titration. Specifically, 17.5 g of hydroxylamine hydrochloride and 6 ml of 0.05% methyl orange were mixed in 994 ml of distilled water to prepare a 0.25 mol/l hydroxylamine hydrochloride solution, which was then titrated to pH 4. 0.1 g of oxidized hyaluronic acid or chondroitin sulfate was dissolved in 25 ml of the solution, and then titrated to pH 4 with 0.1 mol/l sodium hydroxide. The degree of substitution (%) was calculated by the following equation, and the results are shown in tables 8 to 9.

$$\text{Degree of oxidantion (\%)} = \frac{\text{number of moles of CHO}}{\text{number of mols of oxidized glycosaminoglycan}} \times 100 = \frac{\frac{\text{concentration of sodium hydroxide} \times \text{volume of soduim hydroxide} \times 10^{-3}}{\text{weight of oxidized glycosaminoglycan}} \times 100}{\text{amount of glycosaminoglycan repeating unit}} \quad \text{Equation 3}$$

TABLE 8

| DS (%) | HA weight (%) | Oxidant concentration (mM) | Reaction temperature (° C.) | Reaction time (h) |
|---|---|---|---|---|
| 3.7 | 1.0 | 0.8 | 40 | 24 |
| 7.4 | 1.0 | 1.7 | 40 | 24 |
| 15.2 | 1.0 | 2.6 | 40 | 24 |
| 17.7 | 1.0 | 3.3 | 40 | 24 |
| 21.8 | 1.0 | 4.1 | 40 | 24 |
| 35.6 | 1.0 | 5.3 | 40 | 24 |
| 52.8 | 1.0 | 7.8 | 40 | 24 |
| 96.4 | 1.0 | 15.6 | 40 | 24 |

TABLE 9

| DS (%) | HA weight (%) | Oxidant concentration (mM) | Reaction temperature (° C.) | Reaction time (h) |
|---|---|---|---|---|
| 9.8 | 1.0 | 2.2 | RT | 18 |
| 16.6 | 1.0 | 2.8 | RT | 18 |
| 20.8 | 1.0 | 3.4 | RT | 18 |
| 29.2 | 1.0 | 4.3 | RT | 18 |
| 33.9 | 1.0 | 5.6 | RT | 18 |
| 47.2 | 1.0 | 7.3 | RT | 18 |
| 60.0 | 1.0 | 8.4 | RT | 18 |
| 99.2 | 1.0 | 11.0 | RT | 18 |

(2) Preparation of Second Component Having Two or More Amino Groups

Figure 7:
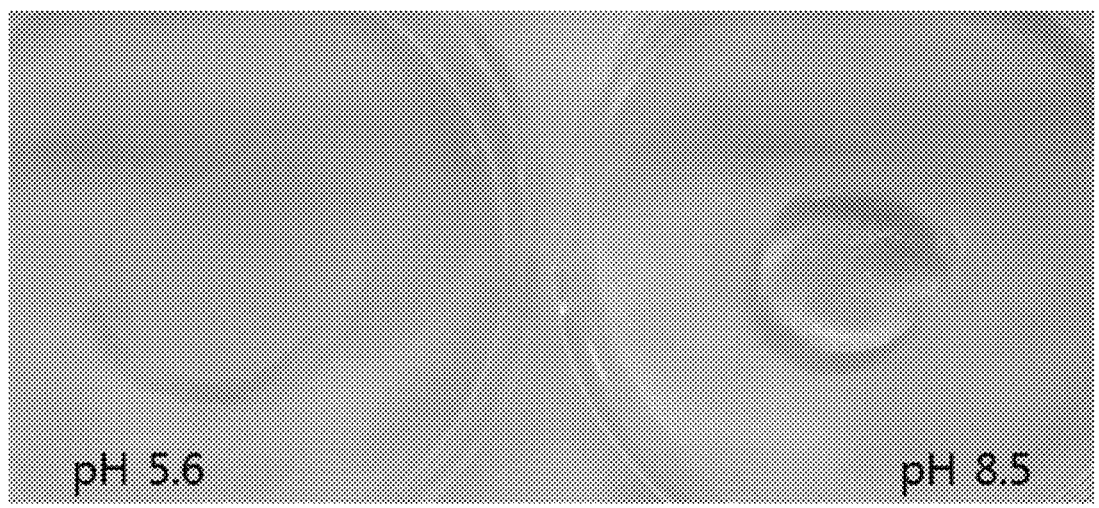
FIG. 7 shows images illustrating the gelation state, gelation time, and gelation depending on pH, of a mixture of an oxidized glycosaminoglycan and a polyamine.

Out of various amino group-containing polyamines, chitosan, protamine, PEI, polylysine, spermine, spermidine, and albumin were typically used as the second component. In order to investigate gelation depending on pH, the powders, which were obtained by adjusting pH in an aqueous solution phase to several ranges (5.5-6.4, 6.5-7.4, 7.5-8.4, 8.5-9.4, 9.5-10.4, and 10.5-11), and then freeze-drying the solution in the same manner as in the oxidized hyaluronic acid/oxidized chondroitin sulfate, were used as the second component. The oxidized hyaluronic acid/oxidized chondroitin sulfate as the first component and a polyamine were mixed. As a result, it was verified that the gelation occurred only at pH of 8.5-11, regardless of the type of polyamine. For example, the gel was formed when the pH of poly-L-lysine was 8.5, but the gel was not formed when the pH thereof was 5.6. In the present test, the formation or not of a gel was determined by the transparency of the gel (transparent; gelation, opaque: non-gelation, FIG. 7).

Example 5: Verification of Optimal Ratio (1) Establishment of Optimal Conditions According to Molecular Weight and Ratio The powder states of oxidized chondroitin sulfate and oxidized hyaluronic acid with a molecular weight of 150-3,000 (1:1) were mixed with a polyamine (PA; selecting and using polylysine of pH 8.5-8.9) according to the degree of oxidation at different mixing ratios, and then the physical properties were verified. 200 μl of sterile distilled water was added to 50 mg of the powders, which were obtained by mixing according to the degree of oxidation at different mixing ratios, and the degree of the sterile distilled water absorbed was verified by the naked eye. The solubility was verified by evaluating the moisture absorption power to be good (+++) when the powder starts to absorb the sterile distilled water within 10 s, moderate (++) within 30 s, and bad (+) over 60 s. In addition, it was verified whether the gelation occurred when the sterile distilled water was added, and the time for gelation was determined. It was verified whether the formed gel was again liquefied, and the time for liquefaction was determined. The results thus verified are shown in the following tables (tables 10 and 11).

As shown in table 11, almost all combinations of the first component and the second component showed desirable results in view of moisture absorption power and the gelation time. Of these, the mixture preparation of 10-50% oxidized chondroitin sulfate+10-40% oxidized hyaluronic acid (150, 1,400 or 3,000 kDa) and the polyamine at a mixing ratio of 1:1 (sample #: 3, 4, 12, 14, 17, 26, 29) showed the best performance (moisture absorption power: +++; and the gelation time: within 30 s). Based on these results, tests were conducted using #14 (named UI-SAH) in the following examples.

TABLE 10

| Sample | DS (%) | Sample | DS (%) | Sample | DS (%) | Sample | DS (%) |
| --- | --- | --- | --- | --- | --- | --- | --- |
| Oxi-CS1 | 11.7 | Oxi-HA1400-1 | 16.0 | Oxi-HA150-1 | 14.6 | Oxi-HA3000-1 | 15.9 |
| Oxi-CS2 | 99.2 | Oxi-HA1400-2 | 35.6 | Oxi-HA150-2 | 33.0 | Oxi-HA3000-2 | 33.1 |
| Oxi-CS3 | 60.8 | Oxi-HA1400-3 | 52.8 | Oxi-HA150-3 | 49.3 | Oxi-HA3000-3 | 48.7 |
| Oxi-CS4 | 42.2 | Oxi-HA1400-4 | 96.4 | Oxi-HA150-4 | 99.4 | Oxi-HA3000-4 | 95.4 |

TABLE 11

| No. | Sample | Moisture absorption power | Gelation time (s) | Liquefaction time (min) |
| --- | --- | --- | --- | --- |
| 1 | Oxi-CS1 + Oxi-HA150K-1 + PA | ++ | 50 | — |
| 2 | Oxi-CS2 + Oxi-HA150K-1 + PA | ++ | 16 | — |
| 3 | Oxi-CS4 + Oxi-HA150K-1 + PA | +++ | 25 | — |
| 4 | Oxi-CS1 + Oxi-HA150K-2 + PA | +++ | 25 | — |
| 5 | Oxi-CS2 + Oxi-HA150K-2 + PA | ++ | 10 | — |
| 6 | Oxi-CS4 + Oxi-HA150K-2 + PA | ++ | 38 | — |
| 7 | Oxi-CS1 + Oxi-HA150K-3 + PA | ++ | 20 | — |
| 7 | Oxi-CS2 + Oxi-HA150K-3 + PA | ++ | 15 | — |
| 8 | Oxi-CS4 + Oxi-HA150K-3 + PA | - | — | — |
| 9 | Oxi-CS1 + Oxi-HA150K-4 + PA | ++ | 25 | — |
| 10 | Oxi-CS2 + Oxi-HA150K-4 + PA | ++ | 15 | — |
| 11 | Oxi-CS4 + Oxi-HA150K-4 + PA | - | — | — |
| 12 | Oxi-CS1 + Oxi-HA1400K-1 + PA | +++ | 25 | — |
| 13 | Oxi-CS2 + Oxi-HA1400K-1 + PA | ++ | 20 | — |
| 14 | Oxi-CS4 + Oxi-HA1400K-1 + PA | +++ | 25 | — |
| 15 | Oxi-CS1 + Oxi-HA1400K-2 + PA | ++ | 25 | — |
| 16 | Oxi-CS2 + Oxi-HA1400K-2 + PA | ++ | 15 | — |
| 17 | Oxi-CS4 + Oxi-HA1400K-2 + PA | +++ | 25 | — |
| 18 | Oxi-CS1 + Oxi-HA1400K-3 + PA | ++ | 26 | — |
| 19 | Oxi-CS2 + Oxi-HA1400K-3 + PA | ++ | 12 | — |
| 20 | Oxi-CS4 + Oxi-HA1400K-3 + PA | ++ | 23 | — |
| 21 | Oxi-CS1 + Oxi-HA1400K-4 + PA | +++ | 34 | — |
| 22 | Oxi-CS2 + Oxi-HA1400K-4 + PA | ++ | 10 | — |
| 23 | Oxi-CS4 + Oxi-HA1400K-4 + PA | +++ | 33 | — |
| 24 | Oxi-CS1 + Oxi-HA3000K-1 + PA | +++ | 32 | — |
| 25 | Oxi-CS2 + Oxi-HA3000K-1 + PA | ++ | 11 | — |
| 26 | Oxi-CS4 + Oxi-HA3000K-1 + PA | +++ | 28 | — |
| 27 | Oxi-CS1 + Oxi-HA3000K-2 + PA | ++ | 27 | — |
| 28 | Oxi-CS2 + Oxi-HA3000K-2 + PA | ++ | 11 | — |
| 29 | Oxi-CS4 + Oxi-HA3000K-2 + PA | +++ | 30 | — |
| 30 | Oxi-CS1 + Oxi-HA3000K-3 + PA | ++ | 30 | — |
| 31 | Oxi-CS2 + Oxi-HA3000K-3 + PA | ++ | 10 | — |
| 32 | Oxi-CS4 + Oxi-HA3000K-3 + PA | +++ | 35 | — |
| 33 | Oxi-CS1 + Oxi-HA3000K-4 + PA | +++ | 50 | — |
| 34 | Oxi-CS2 + Oxi-HA3000K-4 + PA | ++ | 10 | — |
| 35 | Oxi-CS4 + Oxi-HA3000K-4 + PA | +++ | 35 | — |

Example 6: Construction of Rat Hemorrhage Model and Evaluation of Hemostatic Action (1) Hepatolobectomy Model The male SD rat weighing 200-300 g was anesthetized with an intraperitoneal injection of a mixture of ketamine and Rompun, and then the upper part of the center of the belly was incised by about 3-4 cm in a vertical or horizontal direction. The hepatic lobe was exposed through a gap of the incised belly using wet gauze, and the hepatic artery and portal vein were ligated with vascular clips. The site, which was about 1 cm away from the edge of the hepatic lobe, was incised using surgery scissors, and then coated with UI-SAH 50-100 mg. As a control, Arista™ AH (Medafor Inc., USA) was used for coating. After the coating, the clips used for ligation were removed to verify whether bleeding occurred, and then the bleeding amount was measured using sterile gauze.

(2) Nephrectomy Model

The male SD rats weighing 200-300 g was anesthetized with an intraperitoneal injection of a mixture of ketamine and Rompun, and then the right part of the belly was incised by about 3-4 cm in a vertical direction. The kidney was exposed through a gap of the incised belly using wet gauze, and the renal vein and artery were ligated with vascular clips. The site, which was about 1 cm away from the edge of the kidney, was incised using surgery scissors, and then coated with UI-SAH 50-100 mg. As a control, Arista™ AH (Medafor Inc., USA) was used for coating. After the coating, the clips used to ligation were removed to verify whether bleeding occurred, and then the bleeding amount was measured using sterile gauze.

(3) Gastric Mucosectomy Model

The male SD rat weighing 200-300 g was fasted for 24 h, and was anesthetized with an intraperitoneal injection of a mixture of ketamine and Rompun, and then the upper part of the center of the belly was incised by about 3-4 cm in a vertical or horizontal direction. The stomach was exposed through a gap of the incised belly using wet gauze, and the curved portion of the stomach, which has less vessels, was incised by about 3 cm in a horizontal direction to expose the stomach lining. 100 µl of isotonic saline was injected into the stomach lining, and then the stomach lining was resected to have a circular shape with a diameter of about 5 mm, followed by coating with UI-SAH 50-100 mg. As a control, Arista™ AH (Medafor Inc., USA) was used for coating. It was verified whether bleeding occurred at the coated site, and the bleeding amount was measured using sterile gauze.

(4) Portal Vein Hemorrhage Model

The male SD rat weighing 200-300 g was anesthetized with an intraperitoneal injection of a mixture of ketamine and Rompun, and then the upper part of the center of the belly was incised by about 5-6 cm in a vertical or horizontal direction. The portal vein was exposed after the other organs were moved to the left through a gap of the incised belly. Two sites above and below the portal vein were ligated using vascular clips. The portal vein was punched using a 18-gauge needle, and then coated with UI-SAH 50-100 mg. As a control, Arista™ AH (Medafor Inc., USA) was used for coating. After the coating, the clips used for ligation were removed to verify whether bleeding occurred, and then the bleeding amount was measured using sterile gauze.

(5) Test Results

Figure 8:
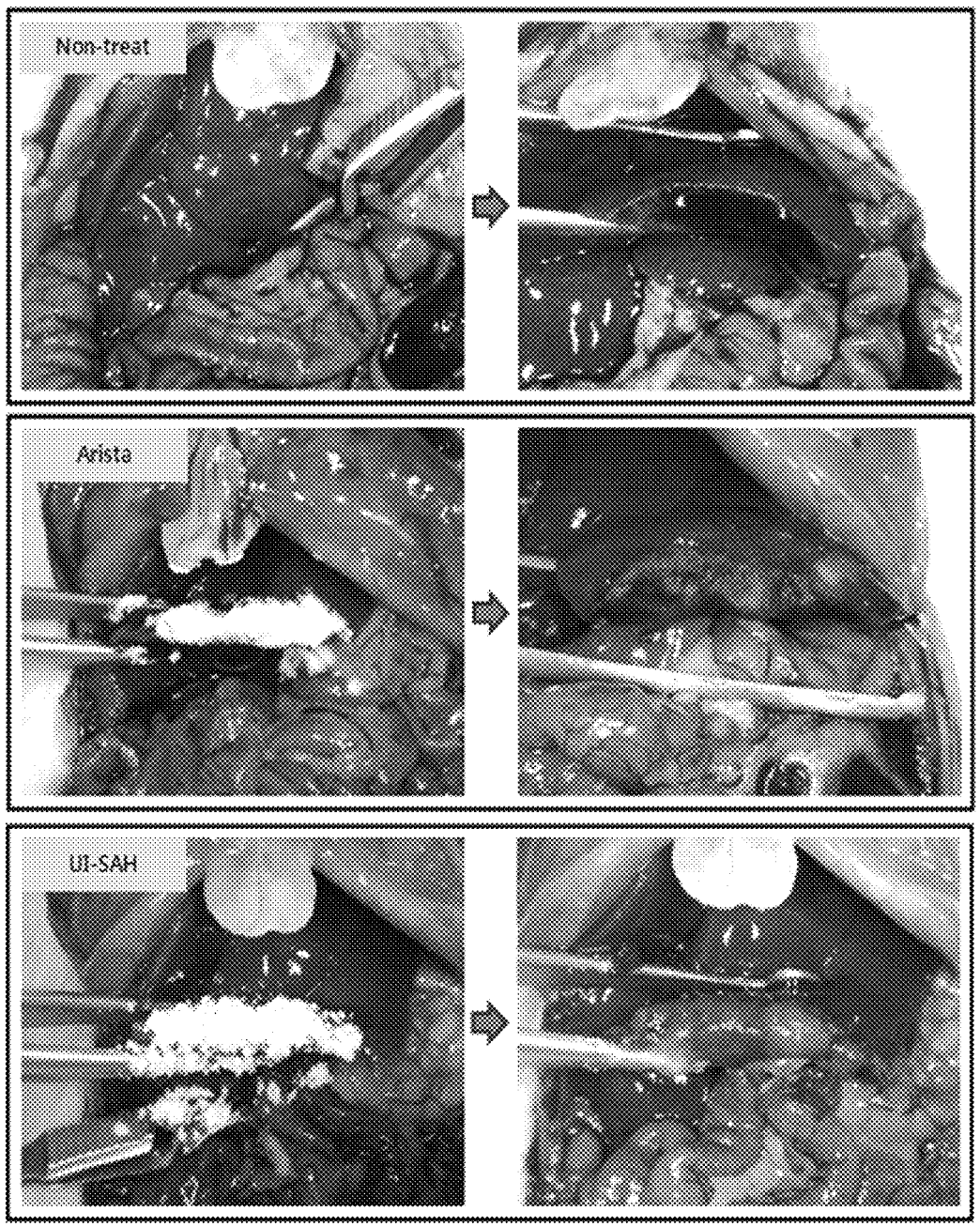
Figure 9:
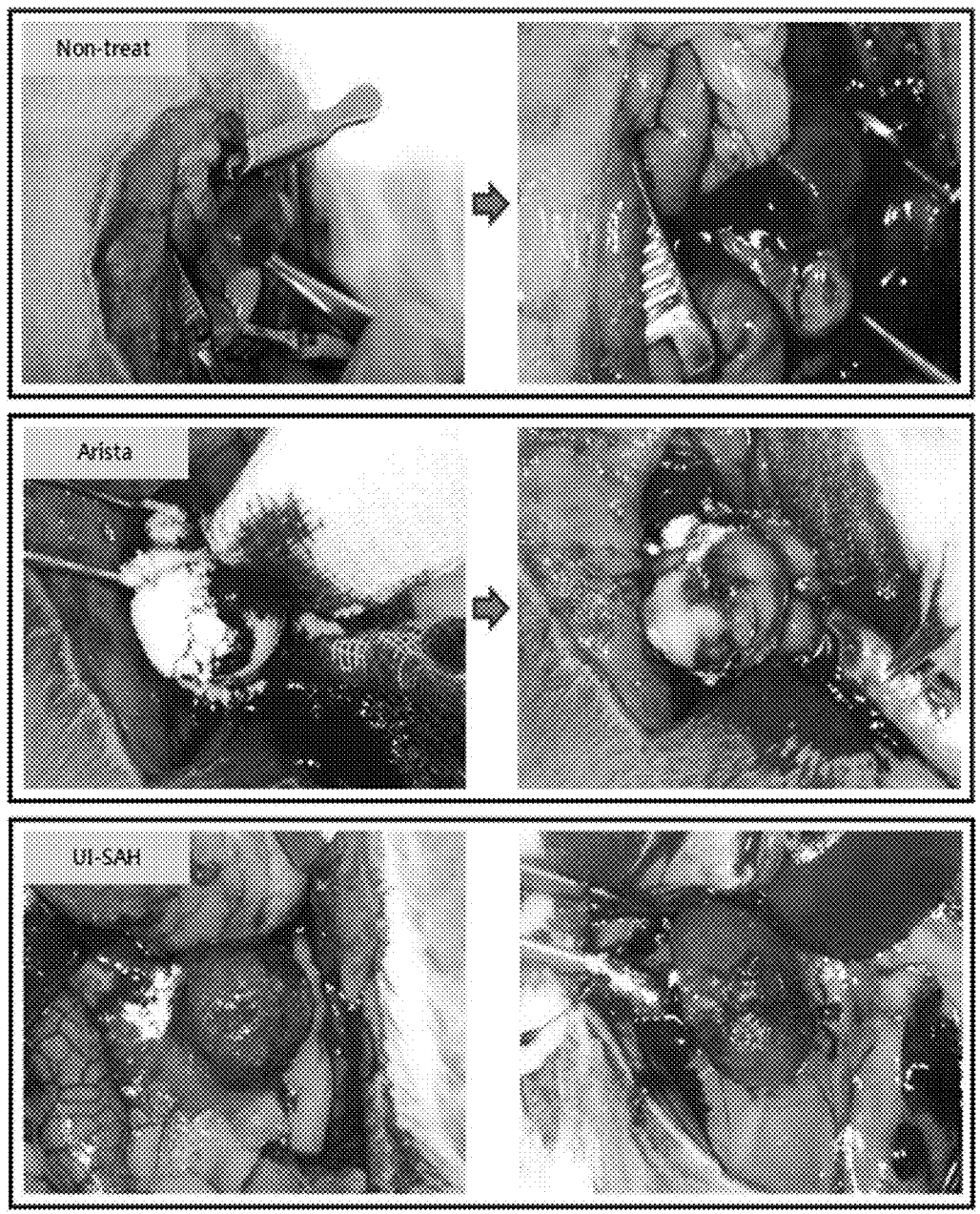
Figure 10:
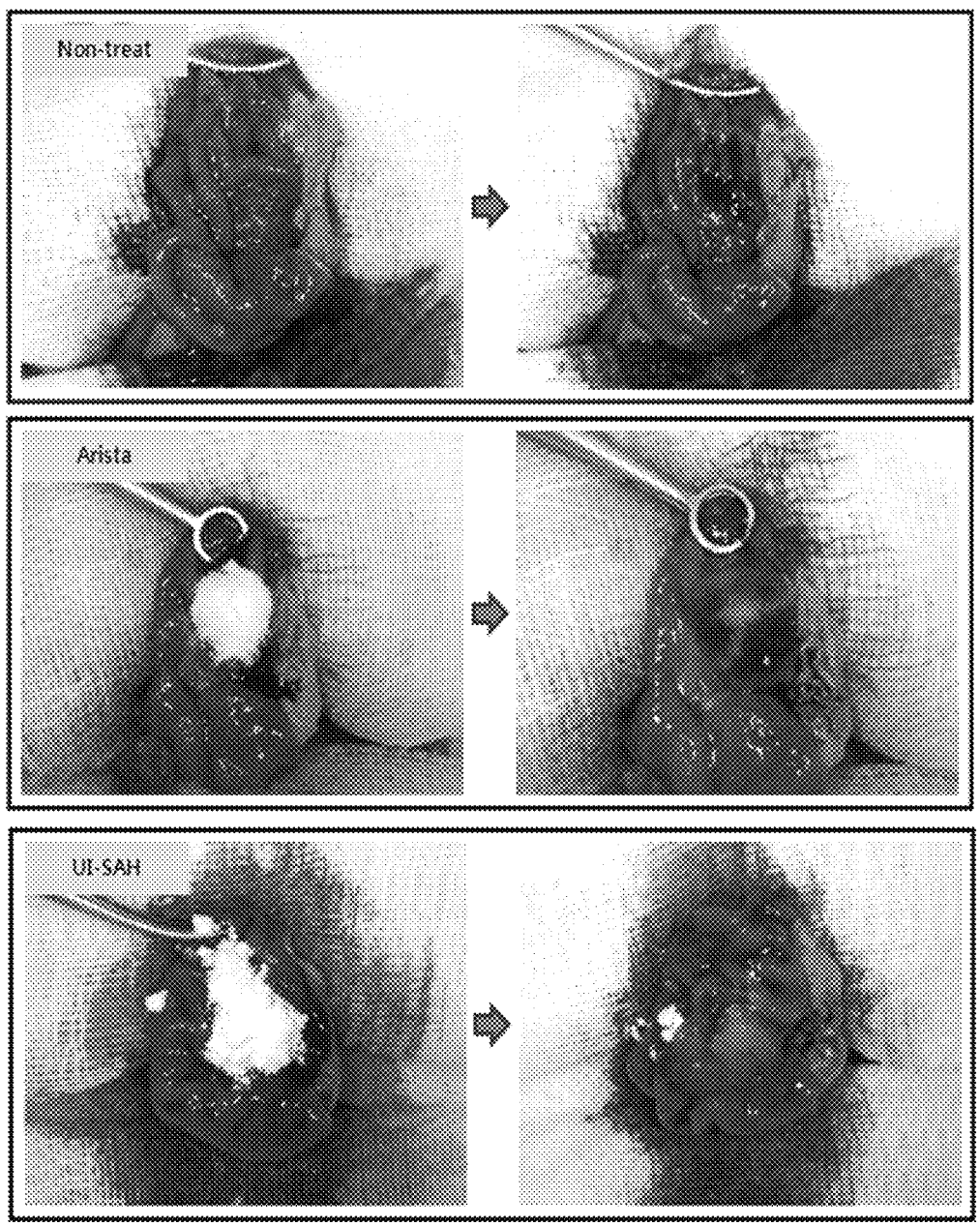
Figure 1:
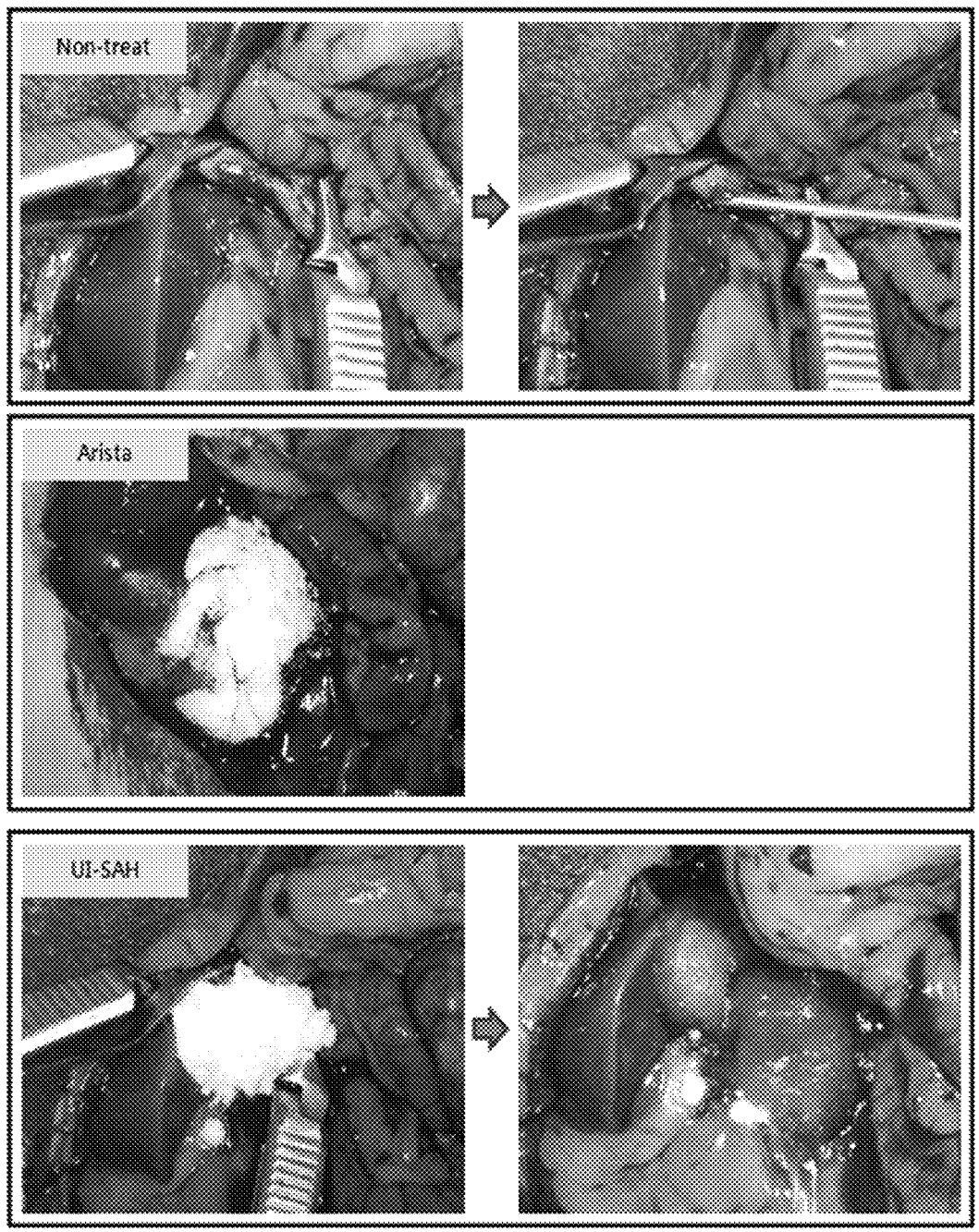
Figure 12:
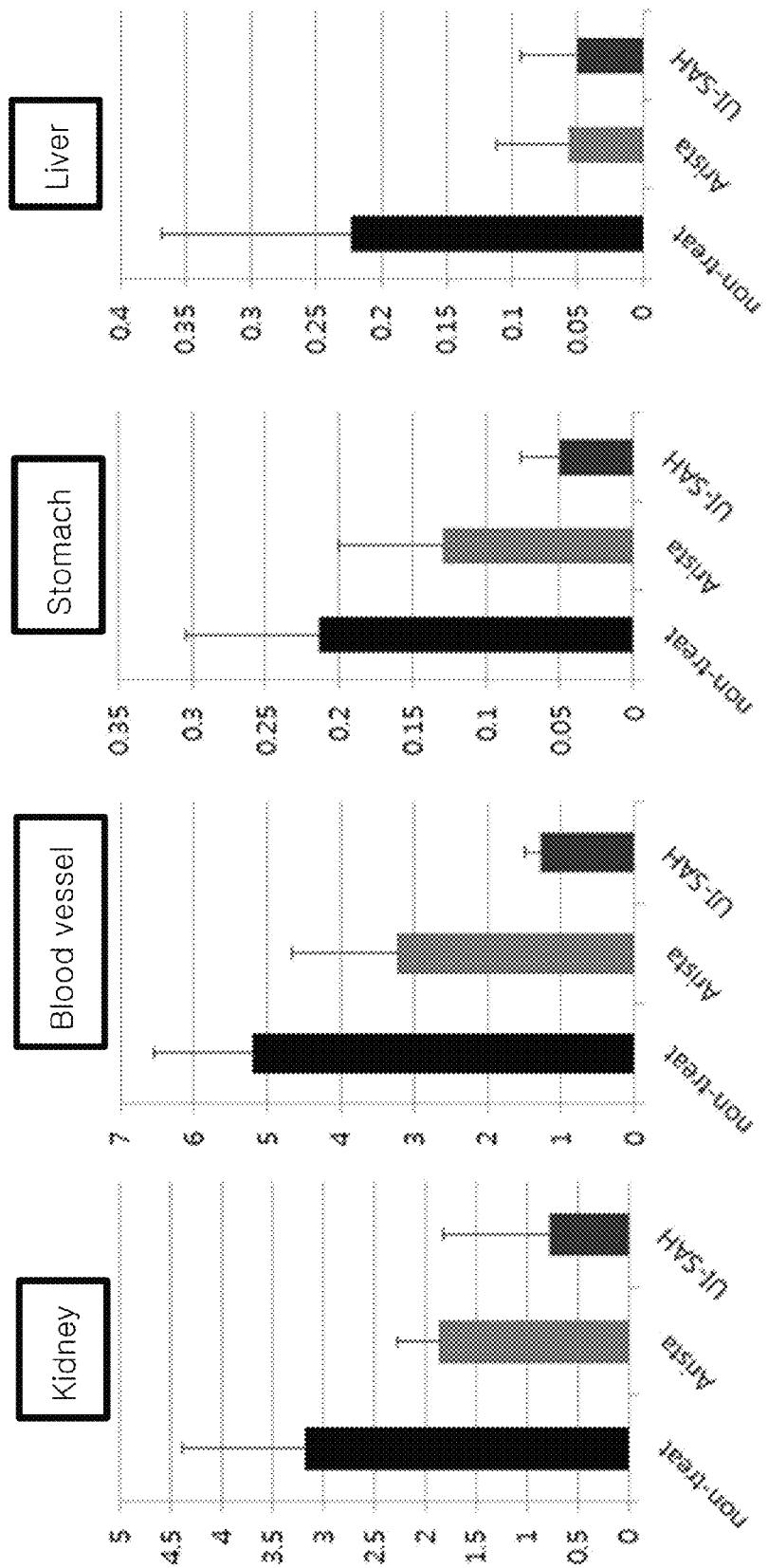
FIG. 12 shows a graph illustrating quantitative results of FIGS. 8 to 11.

Test results are shown in FIGS. 8 and 12. As shown in FIG. 12, the hemostatic effect of the composition of the present invention was more excellent than the control (Arista™ AH).

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A biodegradable medical adhesive or sealant composition, comprising:
   (a) a first component containing two or more different oxidized glycosaminoglycans obtained by oxidation through the introduction of a formyl group; and
   (b) a second component containing a polyamine having two or more amino groups, the pH of the second component in an aqueous solution phase being 8.5-11.0:
   wherein the oxidized glycosaminoglycans are selected from the group consisting of oxidized hyaluronic acid, oxidized chondroitin sulfate, oxidized chondroitin, oxidized dermatan sulfate, oxidized heparan sulfate, oxidized heparin, and oxidized keratan sulfate, and
   wherein the polyamine is selected from the group consisting of polylysine, putrescine, cadaverine, spermidine, spermine, protamine, and polyethylenimine (PEI).

2. The composition of claim 1, wherein the degree of oxidation (%) of the oxidized glycosaminoglycan is 10-99.5%, the degree of oxidation (%) being calculated by the following equation:

$$\text{Degree of oxidation (\%)} = \frac{\text{number of moles of CHO}}{\text{number of mols of oxidized glycosaminoglycan}} \times 100.$$

3. The composition of claim 1, wherein the two or more different oxidized glycosaminoglycans are oxidized hyaluronic acid and oxidized chondroitin sulfate.

4. The composition of claim 3, wherein the degree of oxidation of the oxidized hyaluronic acid is 10-40%, and the degree of oxidation of the oxidized chondroitin sulfate is 10-55%.

5. The composition of claim 1, further comprising a drug having an amine group.

6. A method for performing adhesion, filling, coating, anti-adhesion, wound covering, and hemostasis, on biological tissues, the method comprising a step of applying the biodegradable medical adhesive or sealant composition of claim 1 to biological tissues in need of adhesion, filling, coating, anti-adhesion, wound covering, and hemostasis.

7. The composition of claim 1, wherein the polyamine is selected from the group consisting of polylysine, protamine, and polyethylenimine (PEI).

* * * * *